United States Patent
Doona et al.

(10) Patent No.: US 8,337,717 B2
(45) Date of Patent: Dec. 25, 2012

(54) PROCESS FOR PRODUCING AQUEOUS CHLORINE DIOXIDE FOR SURFACE DISINFECTION AND DECONTAMINATION

(75) Inventors: Christopher J. Doona, Marlboro, MA (US); Florence E. Feeherry, Wellesley, MA (US); Kenneth Kustin, San Diego, CA (US); Maria Curtin, Easton, MA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 467 days.

(21) Appl. No.: 12/008,035

(22) Filed: Jan. 8, 2008

(65) Prior Publication Data

US 2008/0113040 A1    May 15, 2008

Related U.S. Application Data

(63) Continuation-in-part of application No. 11/105,211, filed on Apr. 13, 2005, now Pat. No. 7,625,533, which is a continuation-in-part of application No. 10/988,442, filed on Nov. 10, 2004.

(51) Int. Cl.
*C01B 11/00* (2006.01)
*C01B 11/14* (2006.01)
*C09K 3/00* (2006.01)

(52) U.S. Cl. ......... 252/187.21; 252/187.23; 252/187.24; 252/187.26; 510/108

(58) Field of Classification Search ............. 252/187.21, 252/187.23, 187.24, 187.26
See application file for complete search history.

(56) References Cited

U.S. PATENT DOCUMENTS

| | | | |
|---|---|---|---|
| 4,021,585 A | 5/1977 | Svoboda et al. | |
| 4,362,753 A * | 12/1982 | Barta | 426/332 |
| 4,731,193 A | 3/1988 | Mason et al. | |
| 4,889,654 A | 12/1989 | Mason et al. | |
| 4,908,188 A | 3/1990 | Jefferis, III et al. | |
| 5,407,656 A * | 4/1995 | Roozdar | 423/477 |
| 6,238,643 B1 | 5/2001 | Thangaraj et al. | |
| 6,287,533 B1 | 9/2001 | Khan et al. | |
| 6,399,039 B2 | 6/2002 | Ostgard | |
| 6,440,314 B1 | 8/2002 | Simpson | |
| 6,503,419 B2 | 1/2003 | Klatte | |
| 6,602,466 B2 | 8/2003 | Hamilton et al. | |
| 6,607,696 B1 | 8/2003 | Hamilton et al. | |
| 6,764,661 B1 | 7/2004 | Girard | |
| 2004/0040586 A1 | 3/2004 | Kumar | |
| 2004/0104127 A1 | 6/2004 | Rojas | |
| 2006/0097222 A1 | 5/2006 | Doona et al. | |
| 2006/0099121 A1 | 5/2006 | Doona et al. | |
| 2007/0214577 A1 | 9/2007 | Bianchetti et al. | |

FOREIGN PATENT DOCUMENTS

EP    196075 A2 *   10/1986

* cited by examiner

*Primary Examiner* — Peter F Godenschwager
(74) *Attorney, Agent, or Firm* — Roger C Phillips

(57) ABSTRACT

The present invention provides for a method of generating an aqueous solution comprising chlorine dioxide using a chlorine-containing chemical oxidant; an effector having the capacity to reduce said chlorine-containing chemical oxidant; a chemical reductant; and water, and operating in either batch or continuous-flow modes. In batch mode, the aqueous chlorine dioxide solution can be generated in a sprayer device, a bottle, or a bucket to disinfect objects by spraying and wiping, by pouring, or by immersion, respectively. In continuous-flow mode, the aqueous chlorine dioxide solution can be generated in flow tubes or continuous-stirred tank reactors, then placed inside a suitable sprayer device, bottle, or bucket.

16 Claims, No Drawings

PROCESS FOR PRODUCING AQUEOUS CHLORINE DIOXIDE FOR SURFACE DISINFECTION AND DECONTAMINATION

CROSS-REFERENCE TO RELATED APPLICATION

This is a continuation-in-part of U.S. patent application Ser. No. 11/105,211, filed Apr. 13, 2005 now U.S. Pat. No. 7,625,533,which is a continuation in part of patent application Ser. No. 10/988,442 filed Nov. 10, 2004, in the names of Christopher J. Doona et al., which applications are incorporated in their entirety herein by reference.

STATEMENT OF GOVERNMENT INTEREST

The invention described herein may be manufactured and used by the U.S. Government for governmental purposes without the payment of any royalty thereon.

BACKGROUND OF THE INVENTION

1. Field of the Invention

The present invention relates to lightweight, portable, self-contained devices to disinfect microbiologically contaminated surfaces and/or equipment and whose operation does not require external power sources. The invention, more specifically, relates to such devices that use chemical methods to generate aqueous solutions of disinfectant, which allow immersion of contaminated objects or are dispensed directly or sprayed as a fine mist onto contaminated surfaces for purposes of reducing or eliminating inhabitant microorganisms.

2. Description of the Prior Art

There is a need for on-site decontamination of surfaces, such as the surfaces of military field feeding equipment, food contact surfaces, food processing or handling equipment, and the surfaces of such foods as melons, strawberries, apples, tomatoes, and other sliced or whole fruits and vegetables. This need cannot be met by the application of mild disinfectant solutions in which the disinfecting agent is not powerful enough (for example, hydrogen peroxide or detergent), the concentration of the disinfectant is too dilute to rapidly kill the target microorganisms in sufficient numbers, or the concentration of the lethal chemical agent is too short-lived due to chemical decomposition. In contradistinction, the power-free generation of chlorine dioxide solution meets the requirements for safe, rapid, and easily deployed decontamination system without altering the quality of foodstuffs while minimizing potential hazards to the user, the environment, or consumer of such food-preparation surfaces and equipment and food.

Powerful disinfectant agents such as chlorine, ozone, or chloramines utilize individualized and often heavy equipment that is electrically powered and require special handling. Ozone rapidly degrades chemically and must be continuously generated through specialized electrically powered equipment to maintain an effective lethal dose. During and after the microbial decontamination process, these chemical agents produce harmful by-products in the workplace atmosphere that potentially can be harmful to human health or the environment. Chlorine is an effective disinfectant of waste-waters, but chlorine is also known to react with organic matter to produce harmful chlorinated by-products or carcinogenic compounds such as carbon tetrachloride. Alcoholic solutions require immersion or scrubbing, which may not reach inaccessible surfaces (such as the calyx region of apples or inside the webbing on the surface of cantaloupe rinds), or may be undesirable when contacting food preparation surfaces, foodstuffs, or other consumables.

The basis of the present invention is a novel method that has been developed for the controlled generation of aqueous solutions of chlorine dioxide without requiring the use of power, or where sparks, flames and fire are hazardous, unattainable, or otherwise undesirable. This method is likewise suitable for a lightweight, portable assembly for disinfection of microbiologically contaminated equipment, surfaces, and actual foodstuffs and involves small amounts of safe, dry chemical reagents. The chemical combination that has been developed for this purpose is convenient to carry and mixes readily with water to controllably generate biocidal chlorine dioxide solutions (U.S. patent application Ser. No. 10/988, 442, Publication Number US2006/0097222 A1, Chemical-Combination for Chemical Generation of Disinfectant and Heat, Doona et al.).

This novel chemical combination has been used inside closed containers to generate humid gaseous chlorine dioxide environments (U.S. patent application Ser. No. 11/105,211, Publication Number US2006/0099121 A1, Portable Chemical Sterilizer, Doona et al.). One particular purpose of this technology is the power-free sterilization of medical equipment and surgical instruments in austere environments as may be encountered by military far-forward surgical teams, disaster relief workers, emergency first-responders, or by humanitarian aid workers in third world countries. This technology has also been used under less stringent conditions to eliminate bacterial pathogens such as *Listeria monocytogenes* and *Escherichia coli* from the surfaces of tomatoes without discoloring the fruit, or to inactivate the polyphenoloxidase enzyme in sliced apples, thereby preventing enzymatic browning of the cut apple tissue with exposure to ambient oxygen. The container configuration has been generally aimed at having sufficient size and capacity to hold a standard tray of surgical instruments, but the container configuration can be varied without changing the fundamental principles of operation or procedure for achieving target microbial kills.

Large-scale food-handling equipment and food contact surfaces such as counter tops and cutting boards in need of disinfection cannot always be conveniently removed, separated, or inserted into reasonably sized containers for exposure to a chlorine dioxide environment. However, chlorine dioxide can be used to sanitize surfaces that come into contact with food, and thereby prevent the spread of food-borne illnesses through direct contact or through secondary contamination, by developing an alternative method of dispensing, delivering, or contacting the chlorine dioxide to these contaminated surfaces.

Therefore, an object of this invention is to controllably generate aqueous solutions of biocidal chlorine dioxide using the chemical combination described above, and a number of variants thereof, in a manner different from that used to create humid gaseous chlorine dioxide environments in closed containers for purposes of medical sterilization or produce decontamination, also described above. The chemical combination consists of mixtures of prescribed amounts of sodium chlorite ($NaClO_2$), sodium sulfite ($Na_2SO_3$), sodium hydrogen ascorbate ($C_6H_7O_6Na$), and water that react in either batch mode or in continuous-flow processes to generate an aqueous solution of chlorine dioxide. The batch mode generation of aqueous chlorine dioxide solution can involve the use of a container comprising a lightweight, portable, handheld, closable plastic bottle (rigid plastic or flexible plastic pouch material work equally well) and equipped with an adapter to receive a manually-operated trigger sprayer commonly found on ordinary household cleansers. After generation, the aqueous chlorine dioxide solution can be dispensed directly onto the microbiologically contaminated surfaces from the opened plastic bottle or delivered as a fine mist or aerosol by spraying after closing the bottle with the spray device to achieve the intended surface disinfection or decontamination process. Alternatively, the batch mode generation of aqueous chlorine dioxide solution can involve a container comprising an open bucket that either allows for immersion of contaminated objects such as fresh produce into the disinfecting solution, or into which can be immersed sponges or mops to transfer the chlorine dioxide to the target area for cleaning and disinfection. Another alternative comprises continuous-flow systems comprising tubes or continuous-flow stirred tank reactors that are open to a feed of fresh reagents at a controlled rate and that also allow chemical reaction to take place and produce the aqueous chlorine dioxide disinfectant solution that may then be placed into a bucket, bottle, or sprayer device.

As indicated above, to accomplish these objectives, one cannot simply mimic the mixing procedures described in patent application Ser. No. 11/105,211. Rather, one must determine appropriate variants of the novel chemical combination described in U.S. patent application Ser. No. 10/988,442, select an appropriate sprayer device, bottle, or bucket, and develop a mixing procedure. This disclosure details this novel process, apparatus, and procedure for accomplishing an aqueous chlorine dioxide solution for effective disinfection of foodborne or infectious microorganisms contaminating surfaces.

Disinfectants such as chlorine, ethylene oxide, and fluorine-containing interhalogens are stable but highly reactive chemicals that must be transported in bulky, secure containers to ensure safety. While these chemicals can be transported they are not efficacious in food-preparation environments because of their large weight, size, and inconvenient and ineffective methods of application. Traditional methods of generating chlorine dioxide are too cumbersome, too slow, or too hazardous to allow disinfection of surfaces and foodstuffs.

For example, Svoboda et al. U.S. Pat. No. 4,021,585 teaches the spraying of freshly slaughtered meat carcasses with chlorine dioxide solutions for disinfection without bleaching or discoloring the meat surface. However, the chlorine dioxide is generated "with commercially available equipment . . . ," which would be unsuitable for a kitchen or dining area location, especially those that are transportable for military field feeding, for the reasons indicated above.

Electrochemical methods usually raise the oxidation number of chlorine within a chlorine-containing compound, e.g. oxidizing aqueous chloride solutions, often brines, Rojas, Ser. No. 10/447,572, Publication Number US 2004/0104127. Chemical methods favor the formation of dichlorine gas for this purpose, Jeffries, III et al. U.S. Pat. No. 4,908,188. Alternatively, the oxidation number of chlorine in a chlorine-containing compound can be lowered. For example, reduction of sodium chlorate by hydrogen peroxide, glycerol or sucrose has been suggested, Khan et al. U.S. Pat. No. 6,287,533. These methods require high temperatures and/or catalysts, and are not suitable for safe, rapid generation of chlorine dioxide solutions in a hospital, kitchen or other food processing environment.

Because of chlorine dioxide's potential as a workplace, health clinic or home disinfectant, methods have been developed to circumvent the use of inconvenient and heavy or pressurized cylinder-requiring electrochemical equipment or hazardous strong oxidants such as hypochlorous acid. These methods are based on proton transfer to sodium chlorite by acidification. Acidification-generated chlorous acid disproportionates, producing chloride and chlorate ions and various amounts of chlorine dioxide. The prior art shows that chlorine dioxide so produced can be used for disinfection in food processing plants.

For example, Mason et al. U.S. Pat. Nos. 4,731,193 and 4,889,654 disclose an aqueous foam containing chlorine dioxide for this purpose. The patent claims to mask the odor of chlorine dioxide, because " . . . its strong, unpleasant odor when dissolved in water makes it impossible to spray at concentrations necessary to achieve sanitation." Mason et al. do not teach a new method of generating chlorine dioxide. The patent states that " . . . generating the chlorine dioxide outside the solution and subsequently dissolving it therein" is acceptable. However, in the Mason et al. embodiments that generate the chlorine dioxide in the foam solution, either a water-soluble metal chlorite is acidified, preferably with an organic acid such as citric or oxalic acid, or the chlorite is oxidized by a strong oxidant such as dichlorine or hypochlorous acid. Foam is generated from a surfactant, which may be enhanced with penetrants, non-aqueous solvents, and alkaline cleaners. The odoriferous component in Mason et al. relates to the method of chlorine dioxide generation, which can produce odorous dichlorine and hypochlorous acid gases. In contrast, the present invention yields a dilute aqueous solution of chlorine dioxide that can be dispensed by pouring or spraying a fine mist directly onto and covering all surfaces for purposes of disinfection. Release of gas is minimized, and does not produce a strong or unpleasant odor. The odor, though present, is not pronounced, because of the use of the novel chemical combination (Ser. No. 10/988,442) to controllably produce chlorine dioxide in these circumstances without invoking an acidification process.

The decomposition of chlorous acid is slow and difficult to control. The prior art teaches catalysis and compartmentalization of reagents to speed the reaction and gain some control over it. Girard U.S. Pat. No. 6,764,661 uses compartmentalization and wick means for separating reactants and for transporting water to one or more reactants. The chlorine dioxide is then allowed to diffuse into a separate compartment to constitute the disinfecting solution.

Impregnation of inert zeolite crystals furthers compartmentalization and avoids mixing. Klatte U.S. Pat. No. 6,503,419 teaches impregnation of zeolite crystals with metal chlorite. A second, separate assemblage of zeolite crystals is impregnated with proton-generating species; an acid or a hydrolyzing metal salt such as $CoCl_2$, for example. Activation of the crystals occurs when water is added to the proton-releasing zeolite. Fluid flow carries the acidified solution into the metal chlorite zeolite compartment, where chlorine dioxide gas is generated.

Hamilton et al. U.S. Pat. Nos. 6,602,466 and 6,607,696 teach a method for the controlled delivery of different gases, but take special note of generating and delivering chlorine dioxide gas. These gases cannot be construed as aqueous solutions for reasons mentioned below. Control is exerted by means of successively surrounding one envelope or sachet with another, until an entire sequence of such enclosed pouches-within-pouches has been constructed. This apparatus is claimed to deliver a dose of chlorine dioxide gas to an awaiting volume of water in " . . . 5 to 15 minutes." For most food-handling and processing purposes, this apparatus does not provide controlled production and rapid enough access to a chlorine dioxide solution. The different pouch and envelope surfaces, when not ruptured, act as barriers to diffusion, and the control exerted is to slow down, not speed up the process of forming a disinfectant solution. A similar acidification method used for separating reactants from water, Thangaraj et al. U.S. Pat. No. 6,238,643, suffers from the same drawbacks.

The traditional method to increase the rate of a chemical reaction is through catalysis. Catalysts of the acidification method, however, are expensive and short-lasting, Ostgard U.S. Pat. No. 6,399,039, and it is expected that oxidation-reduction reaction catalysts are likewise expensive and have a short useful duration.

Therefore, it is apparent that there is currently no method available that can controllably generate aqueous chlorine dioxide solutions, preferably in a handheld sprayer device, to sanitize feeding equipment, food contact surfaces, and foodstuffs, all of which can harbor infectious pathogens due to reasons of poor hygiene, contact with contaminated foods, or to bio-terrorism or agri-terrorism. What is needed is a method, operating in either batch or continuous-flow, of generating aqueous disinfectant that is convenient, easy to use, and effective at low doses against microbes. The chemical combination specified in Ser. No. 10/988,442 can be used with appropriate modifications to generate aqueous chlorine dioxide in a sprayer device, in other containers (e.g., bottles or buckets), or by a continuous-flow system. Adjusting the amounts of the dry chemical powders and water specified in Ser. No. 10/988,442 to appropriate levels allows for control of the rate of chlorine dioxide production and optimization of the final concentration of chlorine dioxide in aqueous solution in the sprayer apparatus, and a single sprayer device can then be re-used multiple times for a number of different applications, such as decontaminating food processing or feeding equipment, kitchens, sinks, counter tops, bathrooms or latrines, showers, or fresh produce.

SUMMARY OF INVENTION

With the above and other objects in view, a feature of the present invention is the provision of a novel chemical combination for producing chlorine dioxide, a unique manner of combining these chemical reagents to control the rate and final concentration of chlorine dioxide in aqueous solution so produced, and a container to contain the reagents during mixing and production of the disinfectant while also serving as a container designed to subsequently dispense the generated disinfectant solution either through pouring or spraying as a fine mist or aerosol or for immersing microbiologically contaminated objects for the purposes of eliminating or reducing the presence of contaminating microorganisms.

The preferred embodiment includes a lightweight, portable, power-free apparatus that is closable with a screw-cap or a screw-cap/spray nozzle fixture which accommodates controlled chemical reactions that generate in situ the potent disinfectant chlorine dioxide, a stepwise mixing procedure for creating a dilute aqueous solution, and an opening for distributing the disinfectant to contact contaminated surfaces either by direct pouring or by spraying as a fine mist through a detachable spray nozzle fixture.

The preferred embodiment for this apparatus is a standard rigid plastic bottle used in many commercial household cleaning products with a molded plastic screw-top opening that is closable using a screw-cap fixture equipped with a spray nozzle. The capacity ranges generally from about 400-1000 mL. The bottle's interior volume is capable of accepting the novel chemical combination for producing chlorine dioxide. The production of chlorine dioxide entails adding the appropriate amounts of water and pre-weighed dry chemicals (free or in water soluble packets, such as PVA sachets) to the empty plastic bottle, producing chlorine dioxide through chemical reaction, diluting with the appropriate volume of water to reach a pre-determined final concentration of aqueous chlorine dioxide inside the bottle, then closing the bottle with a screw-cap or screw-cap/spray nozzle fixture.

In an alternative embodiment, the apparatus comprises a plastic bottle made of flexible pouch material with a gusseted bottom that opens upon filling with water to allow the bottle to stand upright and fitted with a screw-cap assembly capable of accepting a screw-cap or a screw-cap/spray nozzle fixture. The production of chlorine dioxide entails adding the appropriate amounts of water and pre-weighed dry chemicals (free or packaged in water-soluble membrane materials that dissolve in the water during the initial mixing, such as PVA sachets) to the empty plastic bottle, producing chlorine dioxide through chemical reaction, diluting with the appropriate volume of water to reach a pre-determined final concentration of aqueous chlorine dioxide inside the bottle, then closing the bottle with a screw-cap or screw-cap/spray nozzle fixture.

The rigid plastic bottle and flexible plastic pouch material can also accommodate several alternative methods for combining the dry chemicals without altering the fundamental mechanism of generating the disinfectant solution. The chemical reagents can be pre-added to either the rigid plastic or the flexible plastic pouch by impregnating them on the interior surface of the plastic material or attaching them with a water soluble adhesive to the interior surface of the plastic that contacts the water. The flexible pouch material offers an additional method for pre-adding and partitioning the chemical reagents into separate compartments that are segregated from the main interior volume by the use of frangible seals. These seals essentially provide sub-compartments within the pouch that can keep the chemical reagents dry and segregated until time of use. Upon squeezing the pouch by hand and applying mild pressures, these seals rupture and empty the reagents into the body of the pouch for subsequent dissolution and mixing in water to controllably produce chlorine dioxide.

The present invention provides a method of generating an aqueous solution comprising chlorine dioxide comprising the steps of: a) combining a chlorine-containing chemical oxidant having the capacity to react and liberate chlorine dioxide; an effector having the capacity to reduce said chlorine-containing chemical oxidant; and a chemical reductant; b) adding a pre-determined quantity of water to the mixture to dissolve the reactants and initiate the production of chlorine dioxide in a concentrated solution; and c) adding additional water to dilute the aqueous solution comprising chlorine dioxide to its final working concentration. The general definitions of the chlorine-containing oxidant, the effector and the chemical reductant are the same as discussed in published U.S. Patent Application 2006/0097222 (U.S. patent application Ser. No. 10/988,442), the disclosure of which is incorporated in its entirety in the present application.

More specifically, the effector can be ascorbic acid, a salt of hydrogen ascorbate, and a salt of ascorbate. Alternatively, the effector can be erythorbic acid and its salts, and tartaric acid and its salts; or a reducing sugar.

The chemical reductant can be disodium sulfite, sodium dithionite, hypophosphorus acid, and iron(II).

The chlorine-containing chemical oxidant can be an alkali metal salt of chlorite or an alkali metal salt of chlorate. More specifically, the alkali metal is sodium.

Preferably, the method of generating an aqueous solution comprising chlorine dioxide uses sodium chlorite as the chlorine-containing chemical oxidant; sodium sulfite as the chemical reductant; and sodium hydrogen ascorbate as the effector. More preferably, the sodium chlorite is in the amount of 1.9-9.4 g; the sodium sulfite is in the amount of 0.4-6.5 g;

and the sodium hydrogen ascorbate is in the amount of 0.7-2.5 g. Most preferably, the water added to the mixture to initiate the production of chlorine dioxide is in the amount of 7.5-30 mL.

As another embodiment of the present invention, the present invention provides for a method of generating an aqueous solution comprising chlorine dioxide comprising the steps of: a) mixing a chemical reductant having the capacity to reduce a chlorine-containing chemical oxidant; an effector having the capacity to reduce the chemical oxidant to liberate chlorine dioxide; and a predetermined amount of water; b) adding to the mixture the chlorine-containing chemical oxidant having the capacity to liberate chlorine dioxide to initiate the production of an aqueous solution of chlorine dioxide; and c) adding additional water to dilute the aqueous solution comprising chlorine dioxide to its final working concentration.

As still another embodiment, the present invention provides for a method of generating an aqueous solution comprising chlorine dioxide comprising the steps of: a) combining a chlorine-containing chemical oxidant having the capacity to react and liberate chlorine dioxide with an organic acid having the capacity to acidify the chlorine-containing chemical oxidant and generate chlorine dioxide; b) adding a pre-determined quantity of water to the mixture to dissolve the reactants and initiate the production of chlorine dioxide as a concentrated solution; and c) adding additional water to dilute the aqueous solution comprising chlorine dioxide to its final working concentration.

Preferably, the aqueous solution comprising chlorine dioxide is produced by any of the above embodiments inside of or placed into a container such as a bucket, a bottle, or other container having a spray nozzle assembly that is capable of spraying the aqueous solution. Alternatively, the aqueous solution comprising chlorine dioxide is produced by a continuous-flow process and then placed in a sprayer device equipped with a spray nozzle assembly that is capable of spraying the aqueous solution, a bottle for dispensing disinfectant solution by pouring, or a bucket allowing immersion of contaminated objects or sponges or mops to transfer the disinfectant to a targeted area.

More specifically, the chemical combination used to effect the controlled production of chlorine dioxide in a small volume of water is an ensemble consisting of sodium chlorite ($NaClO_2$), sodium sulfite ($Na_2SO_3$), and sodium hydrogen ascorbate ($C_6H_7O_6Na$) proportionally related, but generally in reduced quantities, to those described in U.S. patent application Ser. Nos. 11/105,211 and 10/988,442. After the chlorine dioxide is produced by the chemical reaction described above, the solution is diluted with a prescribed volume of water to a pre-determined final concentration of aqueous chlorine dioxide. The addition of this second volume of water does not induce, and may limit, the production of chlorine dioxide, although its primary purposes is intended only to modify the final volume of solution and determine the final working concentration of aqueous chlorine dioxide available for disinfecting microbiologically contaminated surfaces.

DESCRIPTION OF THE PREFERRED EMBODIMENTS

1. Apparatus

The present invention is directed toward a lightweight, handheld, portable apparatus in the form of a convenient handheld plastic bottle equipped with a spray nozzle for carrying out chemical reactions that controllably produce chemical disinfecting agents and dissolving those agents so-produced in aqueous solutions. The decontamination of microbiologically contaminated surfaces such as food handling or military field feeding equipment (sanitization), food contact surfaces in a kitchen environment (disinfection), actual foodstuffs such as fresh produce (effective pasteurization), or military clothing, equipment, vehicles, buildings, or materiel (decontamination) is achieved by dispensing the aqueous disinfectant solution onto the contaminated surface either by pouring directly or spraying as a fine mist from a spray fixture inserted in the bottle.

The preferred use of the portable handheld sprayer involves a chemical combination and mixing procedure that produce a dilute aqueous solution of disinfectant that reduces or eliminates contaminating microorganisms on contact surfaces in sufficient time of exposure. Therefore, there follows below a detailed description of the chemical combination, followed by descriptions of the embodiments of the apparatus in which the chemical combination is activated to produce disinfectant, and a description of the procedure and several tests demonstrating effectuation of the principle of microbial decontamination achieved using the spray method.

The preferred embodiment for mixing the chemical reagents to produce chlorine dioxide, diluting with water to produce a prescribed final concentration, and dispensing by pouring as a solution or spraying as a fine mist or aerosol is a standard rigid plastic bottle with a screw-cap/spray nozzle assembly. Alternatively, a flexible plastic pouch material with a gusseted bottom and a screw-cap assembly woven into the top seam works identically to the hard plastic bottle, and equally well receives the appropriate chemical combinations and volume of aqueous diluent to prepare the disinfectant solution for decontaminating target surfaces, in many cases by simply spraying and wiping. Another alternative container that equally well receives the appropriate chemical combination and water to generate an aqueous chlorine dioxide solution is a bucket that allows for the immersion of contaminated objects such as fruits and vegetables into the disinfectant solution, or transfer of the disinfectant solution to target areas using sponges or mops.

2. Process

The chemical combination in the preferred method for surface decontamination by aqueous chlorine dioxide solution is a mixture of reagents and water that can be varied by proportionately increasing or decreasing the chemical combination given below, or by adjusting the relative proportions of the component reagents, depending on the intended final concentration of chlorine dioxide to be controllably produced. A representative chemical combination used to achieve sterilization with the Portable Chemical Sterilizer (PCS, see U.S. patent application Ser. Nos. 10/988,442 and 11/105,211) consisted of 300 mL $H_2O$ (water), 93 g $NaClO_2$ (sodium chlorite), 63 g $Na_2SO_3$ (sodium sulfite), and 25 g $NaC_6H_7O_6$ (sodium hydrogen ascorbate). The same general ratios as used with the PCS were used to create the aqueous chlorine dioxide solution, but on a scale of reduced quantities of roughly 20-fold. A typical mixture consisted of 15 mL $H_2O$ (water), 4.7 g $NaClO_2$ (sodium chlorite), 0.7 g $Na_2SO_3$ (sodium sulfite), and 1.3 g $NaC_6H_7O_6$ (sodium hydrogen ascorbate). The relative proportions of the reagents were adjusted slightly in some cases, which might be a factor that could help optimize the composition in commercial applications, and still yielded aqueous chlorine dioxide. Chlorine dioxide ($ClO_2$) indicator test strips provided a general range of the estimated concentration.

In Step 1 of the mixing process ("pre-concentration"), small quantities of the reagents were added into a spray bottle (spray handle removed) with a commensurate volume of water (Table 1). In general, with slight variations for each respective composition, after 2-10 minutes, the reaction produces the green-yellow color of chlorine dioxide. The presence of chlorine dioxide was identified and confirmed using UV/V is spectrophotometry (chlorine dioxide shows a characteristic maximum at 360 nm) and the concentration of chlorine dioxide was assayed using commercially available chlorine dioxide indicator test strips. The pre-concentration of the chemical reagents in this manner allowed for kinetics control to manage the time of reaction and concentration of chlorine dioxide produced.

TABLE 1

Representative chemical compositions used in either hard or flexible plastic (Kapak) bottles to generate chlorine dioxide.

| $ClO_2^-$ (g) | Ascorbate (g) | $SO_3^{2-}$ (g) | water (mL) | Water dilution volume (mL) | $ClO_2$ (ppm) indicator strip |
|---|---|---|---|---|---|
| 9.4 | 2.5 | 6.5 | 30 | — | positive |
| 4.7 | 1.3 | 3.2 | 15 | 400 | >100 |
| 4.7 | 1.3 | 1.6 | 15 | 800 | >100 |
| 4.7 | 1.3 | 1.1 | 15 | 800 | >250 |
| 4.7 | 1.3 | 0.7 | 15 | 800 | >250 |
| 4.7 | 1.3 | 0 | 15 | 400 | $ClO_2$ undetected in 10 min |
| 3.9 | 1.3 | 0.7 | 15 | 800 | >100 (also observed spectrophoto- metrically) |
| 1.9 | 0.7 | 0.4 | 7.5 | 800 | >250 |

In Step 2 of the mixing process ("post-reaction dilution"), a commensurate volume of water (400-1000 mL) was added to the plastic spray bottle to dilute the concentration of aqueous chlorine dioxide to the intended final concentration (Table 1). This two-step process ("pre-concentration" and "post-reaction dilution") constitutes a new method of mixing and exerts kinetics control over the process to control the timescale of the reaction of 2-10 minutes. If all of the water were added initially, the reagent concentrations would be initially so dilute that either the reaction would effectively never take place, or it would be too slow for any practical utility.

3. Microbiological Test Results

A 3-strain cocktail of *Staphylococcus aureus* was grown as the test culture. *S. aureus* was chosen as the target microorganism for these demonstration purposes because it forms distinctive black colonies in Petri dishes containing Baird-Parker Agar (BPA) supplemented with Egg Yolk-Tellurite (EYT) that are readily observable. The count of the untreated controls was $2.96 \times 10^8$ cfu/mL.

Test 1, a 0.1 mL aliquot of the cell suspension, was transferred to BPA-EYT in a Petri dish and uniformly distributed on the BPA-YET surface by spread-plating using a glass hockey stick. The BPA-EYT surface was sprayed with 5 squirts from a plastic spray bottle (either rigid plastic or flexible plastic material) containing a fresh solution of aqueous chlorine dioxide. The Petri dish was rotated between squirts to ensure that the disinfectant solution was evenly distributed across the entire inoculated agar surface, and the disinfectant solution was not mechanically spread to enhance contact with the microbes. This application achieved 87% inactivation of target pathogens ($3.89 \times 10^7$ cfu/mL survivors).

Test 2, 1 mL of *S. aureus* cell suspension was mixed with 1 mL of the generated chlorine dioxide solution and the mixture was agitated. A 0.1 mL aliquot of the mixture was transferred to BPA-EYT in a Petri dish, and a glass hockey stick was used to mechanically spread plate the aliquot uniformly across the agar surface. This procedure led to 100% inactivation (0% survivors) of the entire *S. aureus* inoculum.

The above and other features of the invention, including various novel details of the assembly and combinations of parts, will now be more particularly described and pointed out in the claims. The principles and features of this invention may be employed in various and numerous embodiments without departing from the scope of the invention.

What is claimed is:

1. A method of generating an aqueous solution comprising chlorine dioxide comprising the steps of:
    a) combining, within a container having a screw cap for accepting a spray nozzle assembly, a chlorine-containing chemical oxidant having the capacity to react and liberate chlorine dioxide; an effector having the capacity to reduce said chlorine-containing chemical oxidant; and a chemical reductant;
    b) adding a pre-determined quantity of water to the mixture to dissolve the reactants and initiate the production of chlorine dioxide in a concentrated aqueous solution, wherein each of the oxidant, the effector, the reductant and the water are provided in respective quantities that result in aqueous phase chlorine dioxide formation;
    c) pausing for a period of time that ranges from about two minutes to about ten minutes to allow sufficient production of aqueous chlorine dioxide solution; and
    d) thereafter adding additional water to dilute the aqueous solution comprising chlorine dioxide to its final working concentration.

2. The method according to claim 1 wherein the effector is selected from the group consisting of ascorbic acid, a salt of hydrogen ascorbate, and a salt of ascorbate.

3. The method according to claim 1 wherein the effector is selected from the group consisting of erythorbic acid and its salts, and tartaric acid and its salts.

4. The method according to claim 1 wherein the effector is a reducing sugar.

5. The method according to claim 1 wherein the chemical reductant is selected from the group consisting of disodium sulfite, sodium dithionite, hypophosphorus acid, and iron(II).

6. The method according to claim 1 wherein the chlorine-containing chemical oxidant is selected from the group consisting of alkali metal salt of chlorite and alkali metal salt of chlorate.

7. The method according to claim 6 wherein the alkali metal is sodium.

8. The method according to claim 1 wherein the chlorine-containing chemical oxidant is sodium chlorite; the chemical reductant is sodium sulfite; and the effector is sodium hydrogen ascorbate.

9. The method of claim 8 wherein the sodium chlorite is in the range of between 1.9 g and 9.4 g; the sodium sulfite is in the range of between 0.4 g and 6.5 g; and the sodium hydrogen ascorbate is in the range of between 0.7 g and 2.5 g.

10. The method of claim 9 wherein the water added to the mixture to initiate the production of aqueous chlorine dioxide is in the range of between 7.5 mL and 30 mL.

11. The method of claim 8 wherein the mole ratio of sodium chlorite to sodium hydrogen ascorbate to sodium sulfite to water is (6.0 mole ratio sodium chlorite): (1 mole ratio sodium hydrogen ascorbate): (0.9 mole ratio sodium sulfite): (118.1 mole ratio water).

12. The method of claim 8 wherein the mole ratio of sodium chlorite to sodium hydrogen ascorbate to sodium sulfite to water is (7.9 mole ratio sodium chlorite): (1 mole ratio sodium hydrogen ascorbate): (3.9 mole ratio sodium sulfite): (127 mole ratio water).

13. The method of claim 8 wherein the mole ratio of sodium chlorite to sodium hydrogen ascorbate to sodium sulfite to water is (7.9 mole ratio sodium chlorite): (1 mole ratio sodium hydrogen ascorbate): (0.85 mole ratio sodium sulfite): (127 mole ratio water).

14. A method of generating an aqueous solution comprising chlorine dioxide comprising the steps of:
 a) mixing, within a container having a screw cap for accepting a spray nozzle assembly, a chemical reductant having the capacity to reduce a chlorine-containing chemical oxidant; an effector having the capacity to reduce the chemical oxidant to liberate chlorine dioxide; and a pre-determined amount of water;
 b) adding to the mixture the chlorine-containing chemical oxidant having the capacity to liberate chlorine dioxide to initiate the production of an aqueous solution of chlorine dioxide, wherein each of the oxidant, the effector, the reductant and the water are provided in respective quantities that result in aqueous phase chlorine dioxide formation;
 c) pausing for a period of time that ranges from about two minutes to about ten minutes to allow sufficient production of chlorine dioxide; and
 d) thereafter adding additional water to dilute the aqueous solution comprising chlorine dioxide to its final working concentration of greater than about 100 parts per million (PPM).

15. The method of claim 14 wherein the aqueous solution comprising chlorine dioxide is produced inside of or placed into a container having a spray nozzle assembly that is capable of spraying the aqueous solution.

16. A method of generating an aqueous solution comprising chlorine dioxide comprising the steps of:
 a) combining, within a container having a screw cap for accepting a spray nozzle assembly, a chlorine-containing chemical oxidant having the capacity to react and liberate chlorine dioxide with an organic acid having the capacity to acidify the chlorine-containing chemical oxidant and generate chlorine dioxide;
 b) adding a pre-determined quantity of water to the mixture to dissolve the reactants and initiate the production of chlorine dioxide as a concentrated solution, wherein each of the oxidant, the effector, the reductant and the water are provided in respective quantities that enhance aqueous chlorine dioxide formation and reduce gaseous chlorine dioxide formation;
 c) pausing for a period of time that ranges from about two minutes to about ten minutes to allow sufficient production of chlorine dioxide; and
 d) thereafter adding additional water to dilute the aqueous solution comprising chlorine dioxide to its final working concentration of greater than about 100 parts per million (PPM).

\* \* \* \* \*